United States Patent [19]
Dietz

[11] Patent Number: 4,878,502
[45] Date of Patent: Nov. 7, 1989

[54] BREATHING SENSOR

[76] Inventor: Henry G. Dietz, 80 Salisbury Ave., Garden City, N.Y. 11530

[21] Appl. No.: 844,523

[22] Filed: Mar. 27, 1986

Related U.S. Application Data

[63] Continuation-in-part of Ser. No. 646,294, Aug. 31, 1984, abandoned.

[51] Int. Cl.⁴ ............................................. A61F 5/00
[52] U.S. Cl. ................................................. 128/725
[58] Field of Search ............... 128/716, 721, 725, 726; 73/705, 713, 861.47, 49.2, 49.3

[56] References Cited

U.S. PATENT DOCUMENTS

| | | | |
|---|---|---|---|
| 3,081,765 | 3/1963 | Kompelien | 128/721 |
| 3,695,608 | 10/1972 | Hanson | 128/725 |
| 3,898,987 | 8/1975 | Elam | 128/716 |
| 4,241,739 | 12/1980 | Elson | 128/725 |
| 4,259,951 | 4/1981 | Chernack et al. | 128/725 |
| 4,417,589 | 11/1983 | Favaloro | 128/716 |
| 4,495,944 | 1/1985 | Arisson et al. | 128/725 |
| 4,579,124 | 4/1988 | Jentges | 128/725 |

Primary Examiner—William E. Kamm

[57] ABSTRACT

Breathing sensor that monitors the inhalation and exhalation of air by sensing the flow of air from a patient's nostrils or by expansion and contraction of the chest, abdomen, side or back. The respiration sensing is changed to an electrical signal that indicates and provides an output signal for monitoring the breathing function. The sensor comprises a housing with a tubular passage containing a ball, a tube connection, a light source, means for detection when the ball interrupts the light source, and an electronic circuit that provides a breathing indicator and output voltage suitable for use in monitoring the patient's breathing.

2 Claims, 3 Drawing Sheets

BREATHING SENSOR

This is a continuation-in-part application of application Ser. No. 646,294, filed Aug. 31, 1984, now abandoned.

SUMMARY OF THE INVENTION

This invention relates to a sensor that monitors the inhalation and exhalation of air from the nostrils of a patient, and more particularly, to a sensor that is actuated by a pressure as little as 0.005 inches of water column.

There are many devices capable of being actuated by breathing, however these are of high cost and often require electrodes to be placed on the patient's body. My invention is a low cost device that requires no wiring to electrodes, and is passive, requiring only tubing to be connected between sensor and patient. A passive device incurs no hazards which can be associated with an electrical circuit.

A principal object of the invention is to provide a breathing sensor to detect apnea. Apnea is the cessation of respiratory air flow lasting more than ten seconds. It is a serious problem which becomes dangerous, especially in infants, and there exists the possibility of a relationship between prolonged apnea and sudden infant death. In adults it can be the cause of death, and monitoring apnea can help in the diagnosis of upper airway obstructions, congestive heart failure, nervous disorders in the early stages of sleep, etc.

Another principal object of the invention is to detect when a patient stops breathing and approaches death. The sensor makes it possible to monitor patients who might lapse into coma due to the hazards of drug reactions or side effects.

Another principal object of the invention is to provide a simple means of monitoring the patient's breathing by using a nasal cannula. Nasal cannulas are readily available as disposables for the administration of oxygen to patients. The cannula is placed over the ears with its tips in the nostrils. There is usually a sliding sleeve that is adjusted at the back of the head so as to obtain a comfortable fit. The cannula connects the air flow from nasal passages to the sensor by means of tubing.

Another principal object of the invention is that the sensor can be used to indicate the expansion and contraction of the chest, abdomen, side or back by placing an enclosed bag on the bodies surface. The bag is normally held in an inflated state by means of an elastic reaction. The movement of the body due to breathing, results in the elastic reaction being compressed causing the bag to deflate. The inflation and deflation of the bag causes a flow of air which is detected by a sensor connected to the bag by tubing.

Other objects, uses and advantages, will be obvious or become apparent from a consideration of the following detailed description and the application drawings.

However, it is to be distinctly understood that the specific drawing illustrations provided are supplied primarily to comply with the requirements of the Patent Laws, and that the invention may have other embodiments that will be obvious to those skilled in the art, and which are intended to be covered by the appended claims.

DESCRIPTION OF THE PREFERRED EMBODIMENTS

Figure 1:
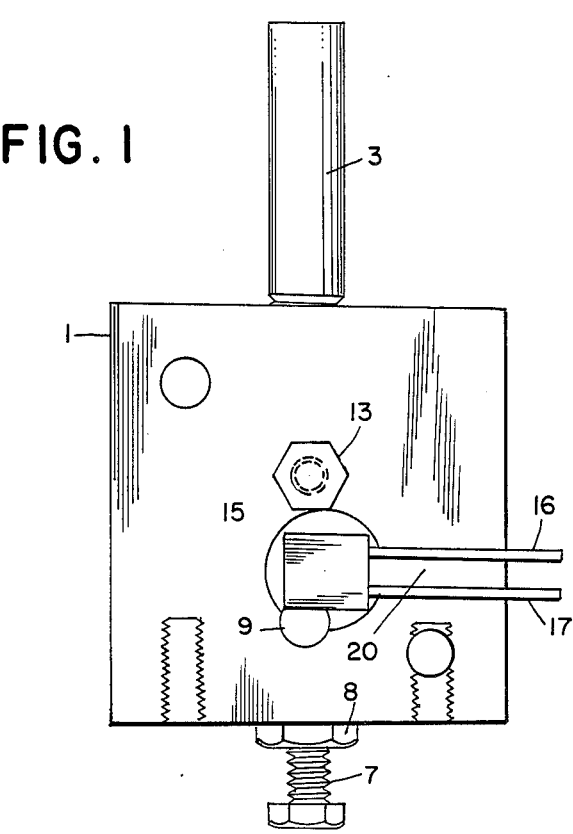
FIG. 1 is a top elevation view of the sensor.
Figure 2:
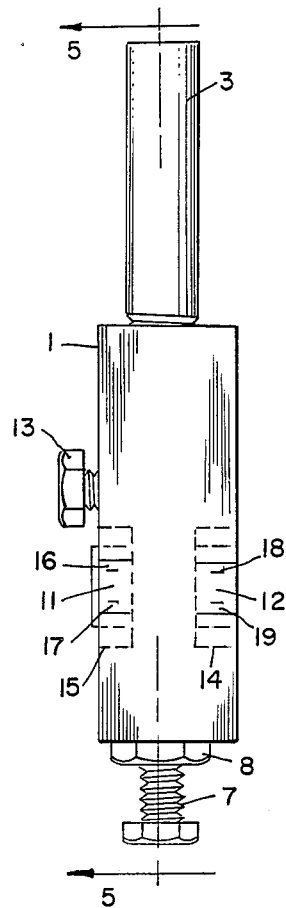
FIG. 2 is a side elevation view of the sensor.

FIGS. 1 and 2 generally indicates a preferred embodiment of the invention which comprises a square housing 1 rectangular in cross section having a main passage or conduit 2 extending longitudinally therethrough. The extremity of one end of the conduit 2 terminates in a threaded bore 4 in the square housing 1 communicating with a threaded tube 3 which allows pressure or vacuum pressure to be applied to the sensor by applying a suitable flexible tube over the projecting end portion of the tubular portion. The extremity of the other end of the conduit terminates in a threaded bore 6 in the square housing 1 to accept a threaded adjustment screw 7. The adjustment screw 7 is threadedly mounted in the square housing 1. To prevent accidental movement of the adjustment screw 7 it is provided with a locknut 8. This adjustment screw 7 has a special significance in that its end is reduced in diameter to allow air to pass without interference through the vent bore 9 in the square housing 1. The adjustment screw 7 provides means for aligning the ball 10 precisely over the lens located in the optoelectronic detector 11, and emitter 12.

The ball 10 is basically of such dimension as to freely roll back and forth in the conduit 2. The specific gravity of the ball 10 can be selected by the type of material it is manufactured from. If plastic is used as the ball 10 material, it is possible to have a range of specific gravity from almost identical to water to only 1/32 the weight of water. The weight of the ball 10 determines its sensitivity, and this weight must be less than the meager forces obtainable from the inhalation air flow. The manufacture of tiny, very-low-density plastic balls is not possible by conventional methods, which involves injection molding the balls and grinding to the exact size. Since a low-density material is mostly air, the balls are crushed by such processing. This difficulty is overcome by taking a bead of styrene containing an expanding agent, placing it in a cavity between a male and female mold, and expanding it with heat into a finished ball. The ball thus made of such low density material is 1/32 the weight of water and is actuated by an inhalation flow of air of approximately 0.003 ounces per square inch of pressure. Such a low density ball 10 will stick to the surface of the tubular passage due to static electricity and/or cohesion. Cohesion is the major problem when the ball hits the stop screw 13, or adjustment screw 7, because intermolecular forces arise creating the attractive force that causes the ball to cling to the stop with a greater force than the force of the inhalation air.

This is overcome in the Dietz invention by coating the ball with graphite which reduces the static charge by making the surfaces of the ball and tubular passageway electrically conductive. The graphite also acts as a barrier to prevent the electron flow from the ball due to the intermolecular forces of cohesion. Mounting the sensor with the passage or conduit 2 perpendicular to the earth's surface with the threaded tube 3 up, will result in that the vacuum applied to the sensor must overcome the pull of gravity on the ball 10. When the sensor is used in this position, the ball 10 will fall and hit the adjustment screw 7 whenever there is no vacuum applied to the sensor. The inhalation breath is always a larger volume of air then the exhalation breath and the effect of gravity must be overcome by the vacuum created by inhalation. Therefore, the exhalation breath is aided by gravity and can be less than the inhalation breath to obtain equal movement of the ball 10 in either direction.

Mounting the sensor with the tubular passage at some angle between perpendicular and horizontal to the earth's surface, results in reducing the pull of gravity on ball 10 and the force necessary to move ball 20 is then that necessary to overcome its inertia as if it were on a horizontal surface. The best sensitivity of the ball 10 for a particular specific gravity can result in some angle located between perpendicular and horizontal mounting.

The movement of ball 10 is restricted by means of the stop screw 13 located in the center of the passage or conduit 2 in square housing 1. Limiting the travel of ball 10 makes the sensor more sensitive to change from the vacuum pressure of inhalation to the pressure of exhalation.

The square housing 1 has two circular recesses 14 and 15 with limited depth, so that they define a chamber to accept the optoelectronic detector 11 and emitter 12. The electrical leads 16, 17, 18, and 19 of the detector 11 and emitter 12 are aligned in a rectangular recess 20 with limited depth.

The square housing 1 is manufactured of a clear transparent material to allow the invisible light from the infrared emitting emitter 12 to pass through it and be detected by a phototransistor detector 11 when the ball 10 moves to a position adjacent to the stop screw 13.

Figure 6:
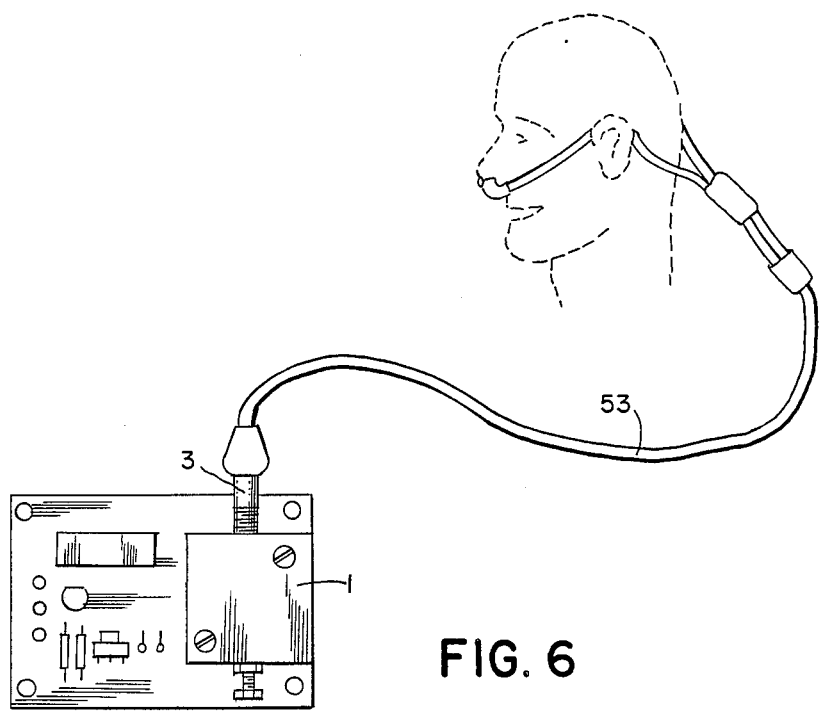
FIG. 6 is a view of a nasal cannula placed in the nostrils of a patient and connected to the inhalation sensor in accordance with the present invention.

The flow of air from the patient's nostrils is directed into the open tips of a cannula 53 which is in direct communication with the sensor by means of being connected with a suitable flexible tube to the threaded tube 3 as shown in FIG. 6. When the patient inhales a vacuum is created that sucks the ball 10 to a position adjacent to the stop screw 13. When ball 10 is in this position, the invisible light from the infrared emitting emitter 12 passes through the square housing 1 and is detected by a phototransistor detector 11. When the patient exhales a pressure is created that pushes the ball 10 to a position adjacent to the threaded adjustment screw 7. When ball 10 is in this position the invisible light from the infrared emitting emitter 12 is blocked by ball 10 and prevented from reaching the phototransistor detector 11.

Figure 3:
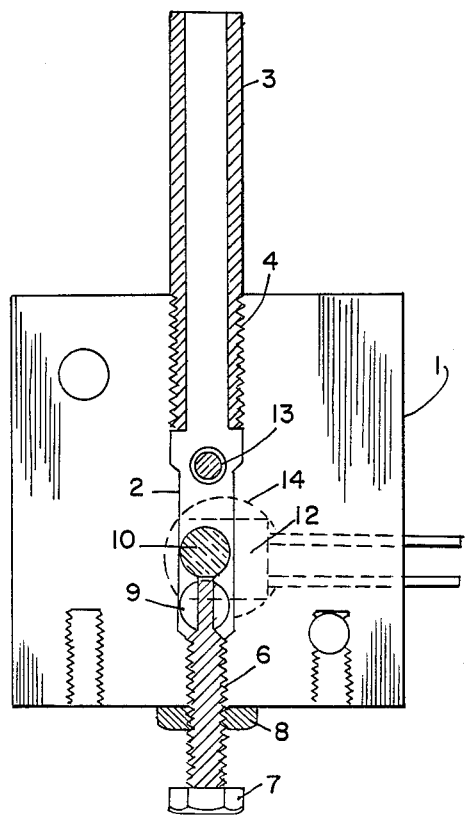
FIG. 3 is a sectional view taken substantially along line 5—5 of FIG. 2.
Figure 4:
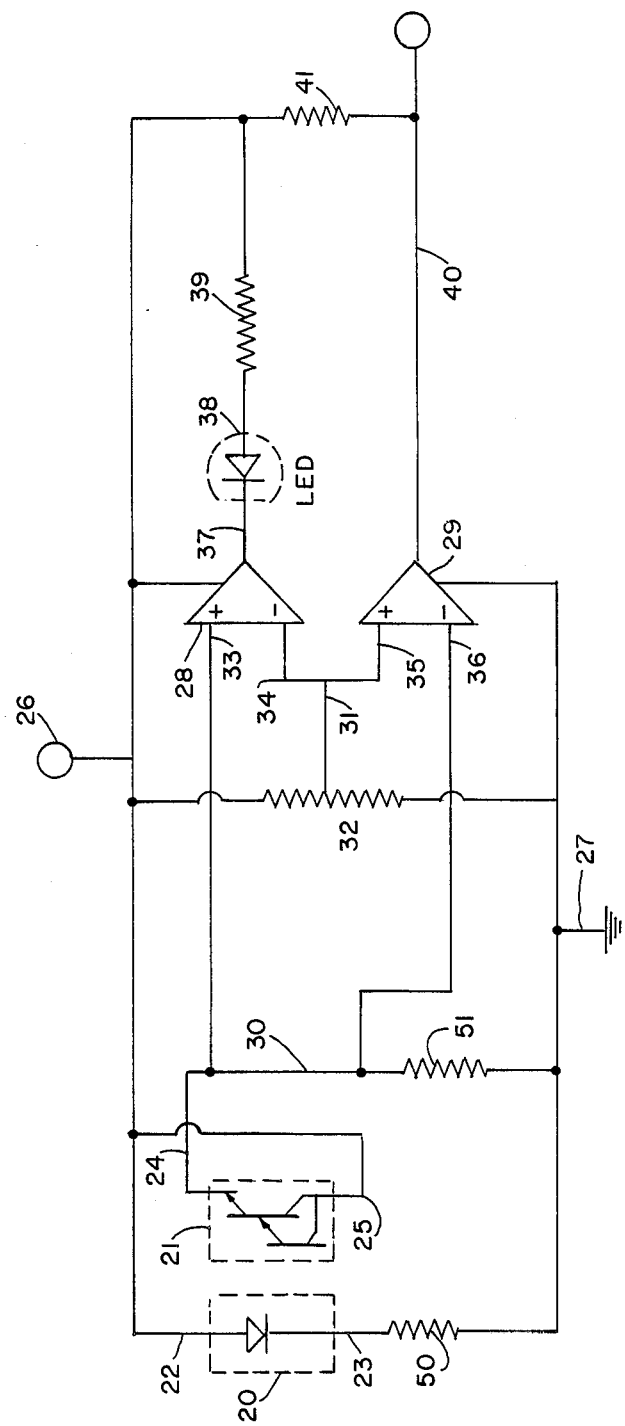
FIG. 4 is a schematic diagram of a circuit responsive to the sensor.
Figure 5:
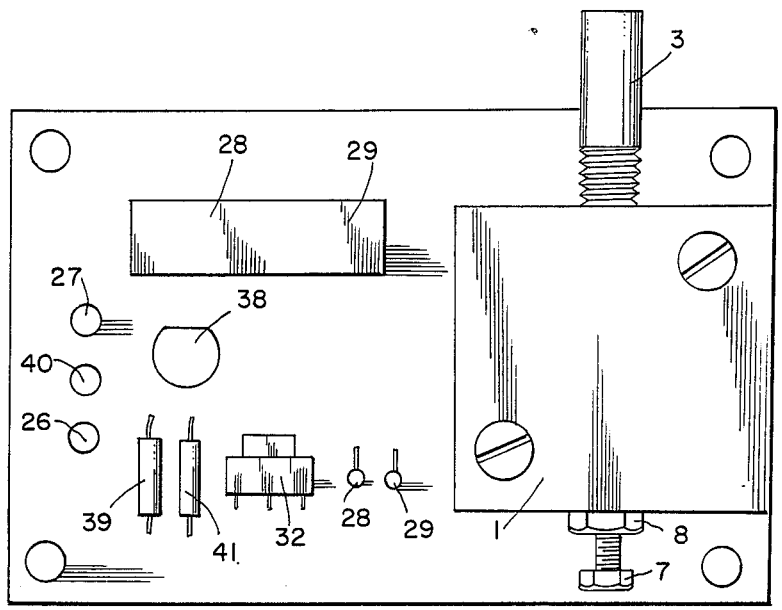
FIG. 5 is a top elevation view of the printed circuit board containing the electronic circuitry and mounting for the housing of FIG. 2.

The sensor is connected to an electronic circuit as disclosed generally in the schematic diagram in FIG. 4. The electronic circuitry of FIG. 4 is mounted on a printed circuit board shown as FIG. 5. This printed circuit board also provides the mounting for housing 1. The purpose of this electronic circuit is to provide a visual indication and a logic high output voltage every time the patient exhales. The circuit in schematic diagram FIG. 4 is supplied with plus 5 volts at terminal 26 and minus 5 volts at ground 27. The emitter 12 on FIG. 2 is the gallium arsenide, infrared emitting diode 20 on the FIG. 4 schematic. The resistor 50 is connected to infrared emitting diode 20 to limit the forward current to an acceptable value. The infrared rays when not interrupted by ball 10 FIG. 3 will be sensed by the silicon darlington connected phototransistor 21.

The resistor 51 connected to the silicon darlington connected phototransistor 21 is an emitter resistor connected to the negative minus 5 volts at ground 27. The output 30 of the silicon darlington connected phototransistor 21 is connected to the voltage comparator 28 and 29. Voltage comparator 28 and 29 have a common connection 31 to variable resistor 32. Variable resistor 32 provides a reference voltage obtained by adjusting it to be between the on and off voltage of the output 30 of the silicon darlington connected phototransistor. This causes the comparators 28 and 29 outputs 37 and 40 to swing between the two states when the ball 10 FIG. 3 is moved in and out to interrupt the infrared light.

The voltage comparator 28 goes into positive or negative saturation according to the difference between the positive voltage input 33 and the negative voltage input 34. The high output 37 is obtained when the ball 10 FIG. 3 does not interrupt the infrared rays resulting in the output 30 connected to input 33 of the comparator 28 giving a high output voltage. The LED 38 has no current flowing through it and displays no brightness. If ball 10 FIG. 3 interrupts the infrared rays, the output 37 of comparator 28 becomes low and the current flows from the terminal 26 through resistor 39 and LED 38 which becomes illuminated when current flows through it.

In like manner voltage comparator 29 gives a logic high output 40 when ball 10 FIG. 3 interrupts the infrared rays. Resistor 41 is connected between the logic output 40 and plus 5 volt at terminal 26.

When the patient exhales output terminal 40 has a high logic output voltage. Likewise the LED 38 is illuminated whenever the patient exhales.

The foregoing description, drawings, and circuit diagram are given merely to explain and illustrate the invention and the invention is not to be limited thereto, except insofar as the appended claims are so limited, since those skilled in the art who have the disclosure before them will be able to make modifications and variations without departing from the scope of the invention.

I claim:

1. A gas flow sensor comprising, a transparent housing, means for defining within said housing a transparent flow path for said gas flow and having a vent in communication with the atmosphere, means for defining a first stop position and other means for defining a second stop position both disposed within a section of the flow path, means for providing communication with said flow path for applying thereto a low value negative pressure from infant nasal airflow to said section of the flow path, a very low density ball made of expanded styrene and freely movable within said flow path in response to said negative pressure and disposed initially at said first stop position and movable to said second stop position in response to said negative pressure when applied to said flow path, an anti-static, anti-static electroconductive coating on said ball, an infrared light source energizable to emit infrared light along a path of infrared light interrupted when said ball is at said first stop position and said infrared light is not interrupted when the ball is at second stop position, detector means for detecting uninterrupted infrared light when the ball moves to said second stop position, and means responsive to detection of said infrared light by said detector means for developing a signal representative of the existence of a negative pressure in said flow path.

2. A gas flow sensor according to claim 1, in which said coating comprises graphite.

* * * * *